United States Patent
Ho

(10) Patent No.: US 11,559,649 B2
(45) Date of Patent: Jan. 24, 2023

(54) SUPPORT MEMBER FOR CUSHION OF RESPIRATORY INTERFACE DEVICE

(71) Applicant: KONINKLIJKE PHILIPS N.V., Eindhoven (NL)

(72) Inventor: Peter Chi Fai Ho, Pittsburgh, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 390 days.

(21) Appl. No.: 16/061,526

(22) PCT Filed: Dec. 5, 2016

(86) PCT No.: PCT/IB2016/057344
§ 371 (c)(1),
(2) Date: Jun. 12, 2018

(87) PCT Pub. No.: WO2017/103724
PCT Pub. Date: Jun. 22, 2017

(65) Prior Publication Data
US 2020/0261680 A1   Aug. 20, 2020

Related U.S. Application Data

(60) Provisional application No. 62/266,834, filed on Dec. 14, 2015.

(51) Int. Cl.
*A61M 16/06* (2006.01)
*B33Y 80/00* (2015.01)
(Continued)

(52) U.S. Cl.
CPC ....... *A61M 16/0622* (2014.02); *B29C 64/106* (2017.08); *B33Y 80/00* (2014.12);
(Continued)

(58) Field of Classification Search
CPC .......... A61M 16/0622; A61M 2207/00; A61M 16/06–0655; B29C 64/106; B33Y 80/00;
(Continued)

(56) References Cited

U.S. PATENT DOCUMENTS 5,343,878 A    9/1994  Scarberry
5,920,915 A *  7/1999  Bainbridge ............ A41D 7/001
                                               2/456
(Continued)

FOREIGN PATENT DOCUMENTS

CA        2845371 A1 *  9/2014  .......... A43B 5/1691
KR      20110024032 A    3/2011
(Continued)

*Primary Examiner* — Justine R Yu
*Assistant Examiner* — Matthew R Moon
(74) *Attorney, Agent, or Firm* — Michael W. Haas

(57) ABSTRACT

A support member for use in a sealing assembly of a patient interface device for delivering a flow of a breathing gas to the airway of a patient. The support member includes: a first end structured to be coupled to a frame member of the patent interface device; a second end structured to sealingly engage the face of a patient or to underlie a sealing flap which is structured to sealingly engage the face of a patient; and a sidewall which extends between the first end and the second end. The sidewall is formed from a plurality of beads of material.

12 Claims, 15 Drawing Sheets

(51) Int. Cl.
  *B29C 64/106* (2017.01)
  *B33Y 10/00* (2015.01)
  *B29K 83/00* (2006.01)
  *B29L 31/00* (2006.01)
(52) U.S. Cl.
  CPC ...... *A61M 2207/00* (2013.01); *B29K 2083/00* (2013.01); *B29L 2031/753* (2013.01); *B33Y 10/00* (2014.12)
(58) Field of Classification Search
  CPC .............. B33Y 10/00; B29L 2031/753; B29K 2083/00; A62B 7/00; A62B 9/00; A62B 9/04; A62B 18/00; A62B 18/02; A62B 18/025
  See application file for complete search history.

(56) References Cited

U.S. PATENT DOCUMENTS

| | | | |
|---|---|---|---|
| 7,662,468 B2* | 2/2010 | Bainbridge | B29C 44/3461 428/304.4 |
| 2002/0185134 A1 | 12/2002 | Bishop | |
| 2004/0089983 A1* | 5/2004 | Jamalabad | B29C 64/106 264/497 |
| 2005/0199239 A1* | 9/2005 | Lang | A61M 16/0616 128/206.24 |
| 2008/0041388 A1* | 2/2008 | McAuley | A61M 16/0616 128/206.24 |
| 2008/0289633 A1 | 11/2008 | Kwok | |
| 2009/0267261 A1 | 10/2009 | Mark | |
| 2011/0162654 A1* | 7/2011 | Carroll | A61M 16/06 128/206.21 |
| 2011/0174310 A1* | 7/2011 | Burz | A61M 16/0622 128/206.24 |
| 2012/0132208 A1* | 5/2012 | Judson | A61M 16/06 128/205.25 |
| 2013/0139822 A1 | 6/2013 | Gibson | |
| 2013/0291409 A1* | 11/2013 | Reinhardt | A43B 5/00 36/30 R |
| 2014/0326246 A1* | 11/2014 | Chodkowski | A61M 16/06 128/206.24 |
| 2015/0035200 A1 | 2/2015 | Karpas | |
| 2015/0040428 A1* | 2/2015 | Davis | B29D 35/142 12/146 B |
| 2015/0096426 A1 | 4/2015 | Culver | |
| 2015/0273170 A1* | 10/2015 | Bachelder | A61M 16/0611 264/129 |
| 2016/0053410 A1* | 2/2016 | Sterman | D02G 3/04 57/244 |

FOREIGN PATENT DOCUMENTS

| | | |
|---|---|---|
| WO | WO2009062265 A1 | 5/2009 |
| WO | WO2011003128 A1 | 1/2011 |
| WO | WO2014075797 A1 | 5/2014 |
| WO | WO2015170997 A1 | 11/2015 |

* cited by examiner

SUPPORT MEMBER FOR CUSHION OF RESPIRATORY INTERFACE DEVICE

CROSS-REFERENCE TO RELATED APPLICATIONS

This patent application claims the priority benefit under 35 U.S.C. § 371 of international patent application No. PCT/IB2016/057344, filed Dec. 5, 2016, which claims the priority benefit under 35 U.S.C. § 119(e) of U.S. Provisional Application No. 62/266,834, filed on Dec. 14, 2015, the contents of which are herein incorporated by reference.

BACKGROUND OF THE INVENTION

1. Field of the Invention

The present invention pertains to a support member for use in a respiratory interface device in delivering a flow of breathing gas to a user. The present invention also pertains to a respiratory interface device for delivering a flow of breathing gas to a user including a support member. The present invention also pertains to a method of forming a support member for use in a respiratory interface device for delivering a flow of breathing gas to a user.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is OSA. Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the patient's nose and mouth, or a full face mask that covers the patient's face. Such patient interface devices may also employ other patient contacting components, such as forehead supports, cheek pads and chin pads. The patient interface device is connected to a gas delivery tube or conduit and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such masks are typically worn for an extended period of time, a variety of concerns must be taken into consideration. For example, in providing CPAP to treat OSA, the patient normally wears the patient interface device all night long while he or she sleeps. One concern in such a situation is that the patient interface device is as comfortable as possible, otherwise the patient may avoid wearing the interface device, defeating the purpose of the prescribed pressure support therapy. It is also important that the overall size of the interface device be minimized, so as to not be overly cumbersome on the face of the patient.

Historically, interface devices are produced in several sizes in order to accommodate the wide variety of facial sizes and structures present in the population. As the number of mask sizes provided increases, so does the costs associated with manufacturing, stocking, etc. It can thus be appreciated that the concept disclosed herein provides interface devices which are able to be readily created and/or are able to be readily customized to produce a better fit.

SUMMARY OF THE INVENTION

Accordingly, it is an object of the present invention to provide an interface device which can be readily produced and custom fit to a particular user. This object is achieved by providing a support member for use in a cushion of a patient interface device for delivering a flow of a breathing gas to the airway of a patient. The support member comprises: a first end structured to be coupled to a frame member of the patent interface device; a second end structured to sealingly engage the face of a patient or to underlie a sealing flap which is structured to sealingly engage the face of a patient; and a sidewall which extends between the first end and the second end, wherein the sidewall is formed from a plurality of beads of material.

The plurality of beads of material may comprise at least one bead having a first cross-sectional area and at least a second bead having a second cross-sectional area different from the first cross-sectional area.

The second cross-sectional area may be a different size than the first cross-sectional area.

The second cross-sectional area may be a different shape than the first cross-sectional area.

The plurality of beads of material may comprise at least one bead formed from a first material and a second bead formed from a second material different than the first material.

At least some beads of the plurality of beads of material may be disposed in a manner which defines at least one void within the sidewall.

The at least one void may be positioned within the sidewall so as to be disposed adjacent the bridge of the patient's nose when the support member is disposed on the face of the patient.

The at least one void may be positioned within the sidewall so as to be disposed adjacent the lower lip of the patient when the support member is disposed on the face of the patient.

The at least one void may comprise a first void and a second void, wherein the first void is positioned within the sidewall so as to be disposed adjacent a first side of the patient's mouth when the support member is disposed on the face of the patient, and wherein the second void is positioned within the sidewall so as to be disposed adjacent a second side, opposite the first side, of the patient's mouth when the support member is disposed on the face of the patient.

The first end may comprise a pre-molded base portion to which the sidewall is coupled and the pre-molded base may be structured to be coupled to a frame member of the patient interface device.

It is yet another object of the present invention to provide a patient interface device for delivering a flow of breathing gas to the airway of a patient. The interface device comprises a rigid frame member and a sealing assembly having a support member as previously described.

Yet a further object of the present invention is to provide a method of forming a support member for use in a sealing assembly of a patient interface device for delivering a flow of a breathing gas to the airway of a patient. The method comprises: applying a first bead of a first settable material in a first predetermined pattern on a working form and applying a second bead of a second settable material in a second predetermined pattern adjacent the first bead, wherein at least one of: the first bead has a cross-sectional area different than the second bead, the second settable material is different from the first settable material, or the second bead is applied spaced a distance from the first bead so as to form a void there between.

The working form may comprise a work surface.

The working form may comprise a pre-formed base portion which is structured to be coupled to a frame member of the patient interface device.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
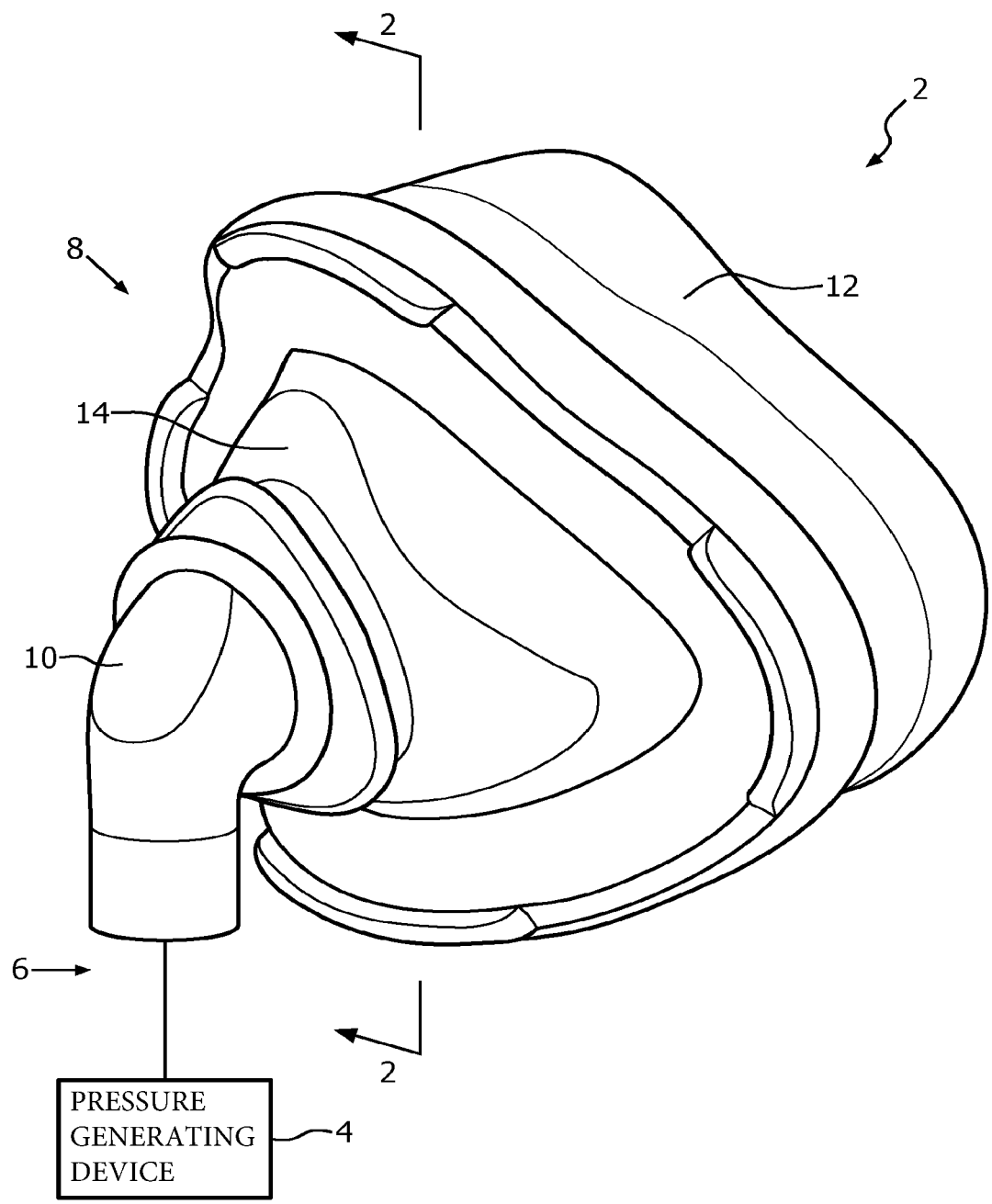
FIG. 1 is a front isometric view of a patient interface device and a portion of a conduit shown connected to a gas flow/pressure generating system (shown schematically) to form a system adapted to provide a regiment of respiratory therapy to a patient according to one exemplary embodiment of the invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As used herein, the word "patient" or "user" shall be used interchangeably to refer to the person to which the interface device is delivering a flow of breathing gas.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

As used herein, the word "bead" shall be used to refer to a quantity of material which has been dispensed in a controlled manner. Typically, a "bead" of material has a generally circular cross-section (although other cross-sections may be employed without varying from the scope of the present invention) and extends a distance in a direction perpendicular to said cross-section.

A system 2 adapted to provide a regimen of respiratory therapy to a patient according to one exemplary embodiment of the invention is generally shown in FIG. 1. System 2 includes a pressure generating device 4 (shown schematically), a delivery conduit 6 (shown partially schematically), and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and user interface device 8 are often collectively referred to as a patient circuit.

A BiPAP® device is a bi-level device in which the pressure provided to the patient varies with the patient's respiratory cycle, so that a higher pressure is delivered during inspiration than during expiration. An auto-titration pressure support system is a system in which the pressure varies with the condition of the patient, such as whether the patient is snoring or experiencing an apnea or hypopnea. For present purposes, pressure/flow generating device 4 is also referred to as a gas flow generating device, because flow results when a pressure gradient is generated. The present invention contemplates that pressure/flow generating device 4 is any conventional system for delivering a flow of gas to an airway of a patient or for elevating a pressure of gas at an airway of the patient, including the pressure support systems summarized above and non-invasive ventilation systems.

In the exemplary embodiment illustrated in FIG. 1, patient interface device 8 is depicted as a nasal/oral mask which includes a user sealing assembly 12 coupled to a generally rigid frame member 14 which is coupled to conduit 6 via fluid coupling conduit 10. However, it is to be appreciated that other types of patient interface devices, such as, without limitation, a nasal mask or a full face mask, which facilitates the delivery of the flow of breathing gas to the airway of a user, may be substituted for patient interface device 8 while remaining within the scope of the present invention. It is also to be appreciated that conduit 6 may be directly coupled to patient interface device 8 without the use of any intermediary coupling, such as conduit 10.

Figure 2:
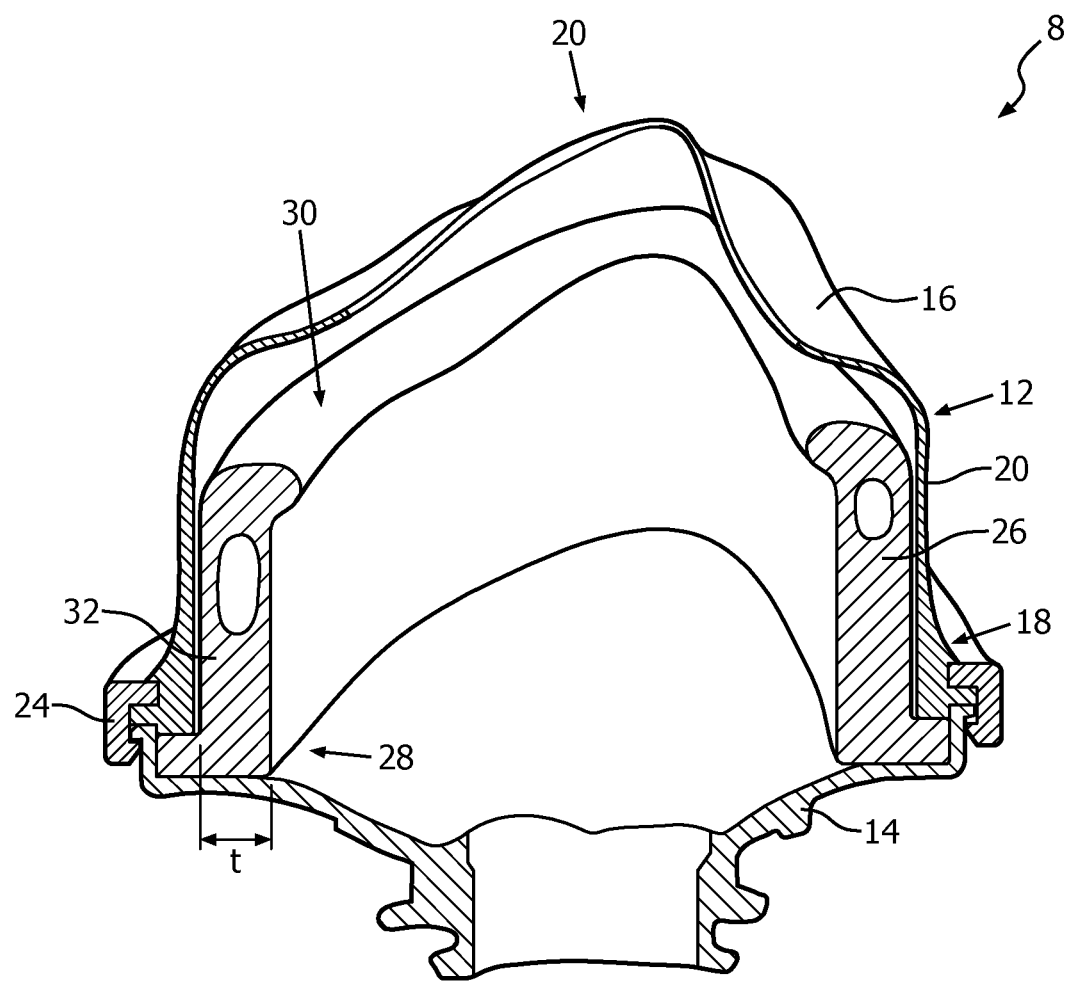
FIG. 2 is a sectional view of the patient interface device of the system of FIG. 1 taken along line 2-2 of FIG. 1.
Figure 3:
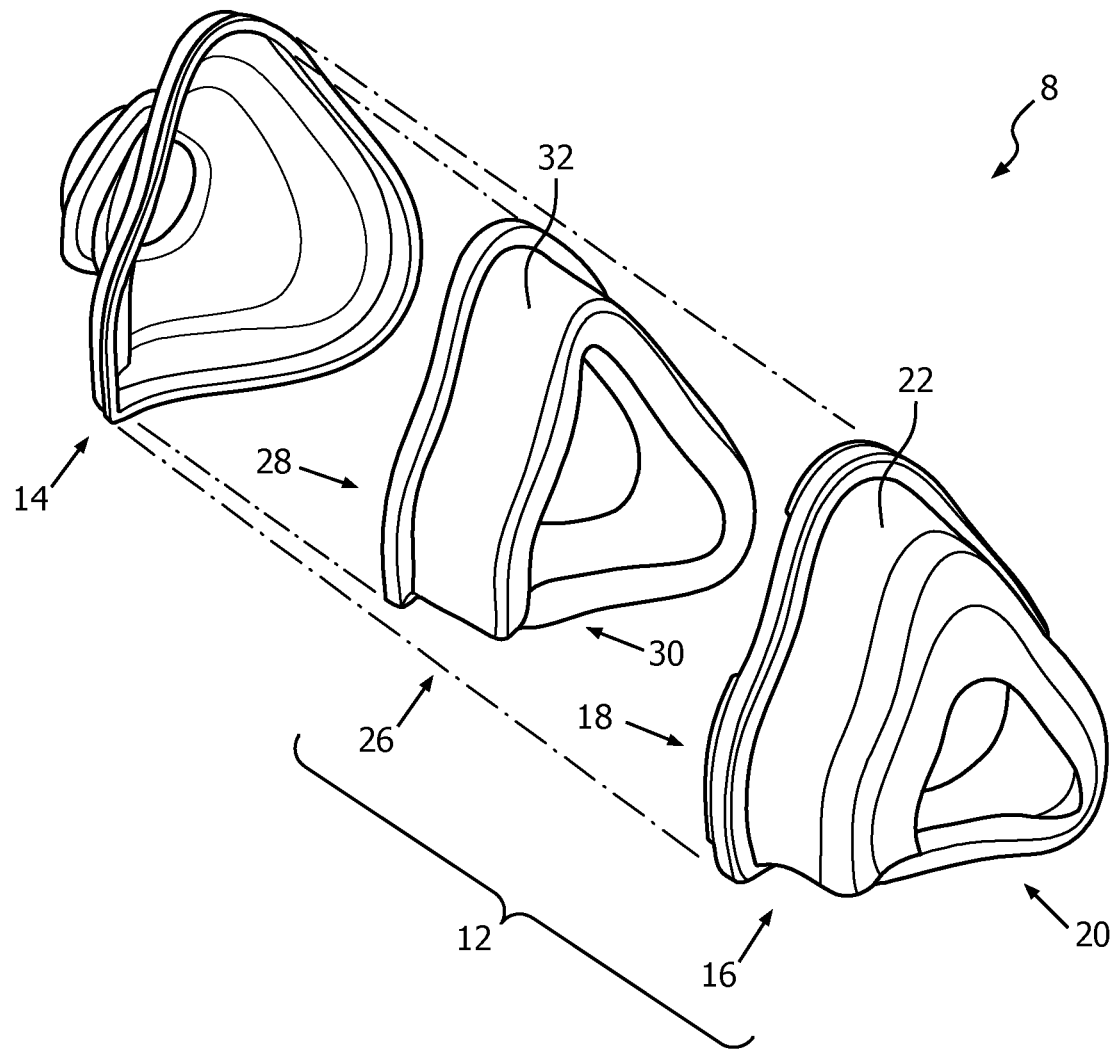
FIG. 3 is a rear isometric exploded view of the patient interface device of FIGS. 1 and 2.

Referring to FIGS. 2 and 3, which, respectively, show sectional and exploded views of patient interface device 8 of FIG. 1, sealing assembly 12 is of a modular design and includes a sealing flap 16 having a first end 18 which is structured to engage and be coupled to frame member 14, an opposite second end 20 which is structured to sealingly engage the face of a user (not shown) about one or more of the oral and/or nasal orifices of the user, and a continuous sidewall 22 which extends between first end 18 and second end 20. Sealing flap 16 is typically formed from a thin pliable material (e.g., without limitation, silicone) so as to generally adapt to, and seal against, the contours of a user's face. In order to assist in coupling sealing flap 16 to frame member 14, sealing flap 16 may further include a retention ring 24 which generally couples about the periphery of first end 18 and at least a portion of frame member 14. Alternatively, sealing flap 16 may be formed such that first end 18 directly couples to frame member 14 without the use of any other coupling elements.

Sealing assembly 12 further includes a support member 26 which generally underlies sealing flap 16 and provides structural support and a predetermined amount of rigidity to sealing assembly 12 while also functioning to keep sealing flap 16 pressed against the user's face. Support member 26 includes a first end 28 which is structured to engage a portion of frame member 14, an opposite second end 30 which generally underlies second end 20 of sealing flap 16, and a continuous sidewall 32 which extends between first end 28 and second end 30. As can be readily appreciated from the sectional view of FIG. 2, support member 26 is typically formed with sidewall 32 having a greater thickness t than sealing flap 16 so as to be of greater rigidity than sealing flap 16.

Figure 2A:
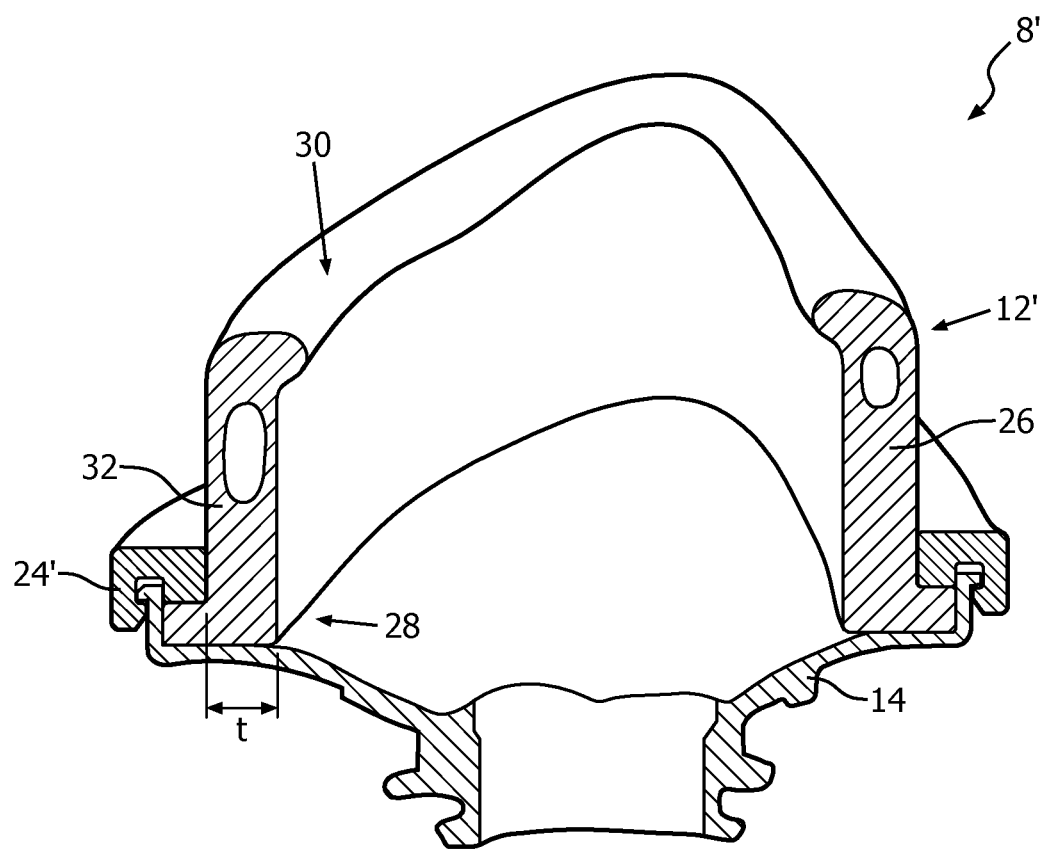
FIG. 2A is a sectional view of an alternate version of the patient interface device for use in the system of FIG. 1 taken along a similar line as line 2-2 of FIG. 1.

A cross-sectional view of an alternative sealing assembly 12' in accordance with one exemplary embodiment of the invention is shown in FIG. 2A as a portion of another patient interface device 8' (which is generally similar to patient interface device 8). Unlike sealing assembly 12, sealing assembly 12' does not utilize a sealing flap, such as sealing flap 16 previously discussed. Instead, sealing assembly 12' utilizes support member 26 as the main component, and thus opposite second end 30 of support member 26 is positioned and structured to sealingly engage the face of a user. Sealing assembly 12' may further include a retention ring 24' which generally couples about the periphery of first end 28 of support member 26 and at least a portion of frame member 14. Alternatively, support member 26 may be formed such that first end 28 thereof directly couples to frame member 14 without the use of any other coupling elements.

It is to be appreciated that such designs of sealing assemblies 12 and 12' allow for the potential customization of such assembly to the particular facial structures of a patient by customizing one, or both of sealing flap 16 or support member 26. FIGS. 4-7 illustrate a system 40 and portions thereof for forming a support member, such as support member 26, in accordance with one exemplary embodiment of the present invention.

Figure 4:
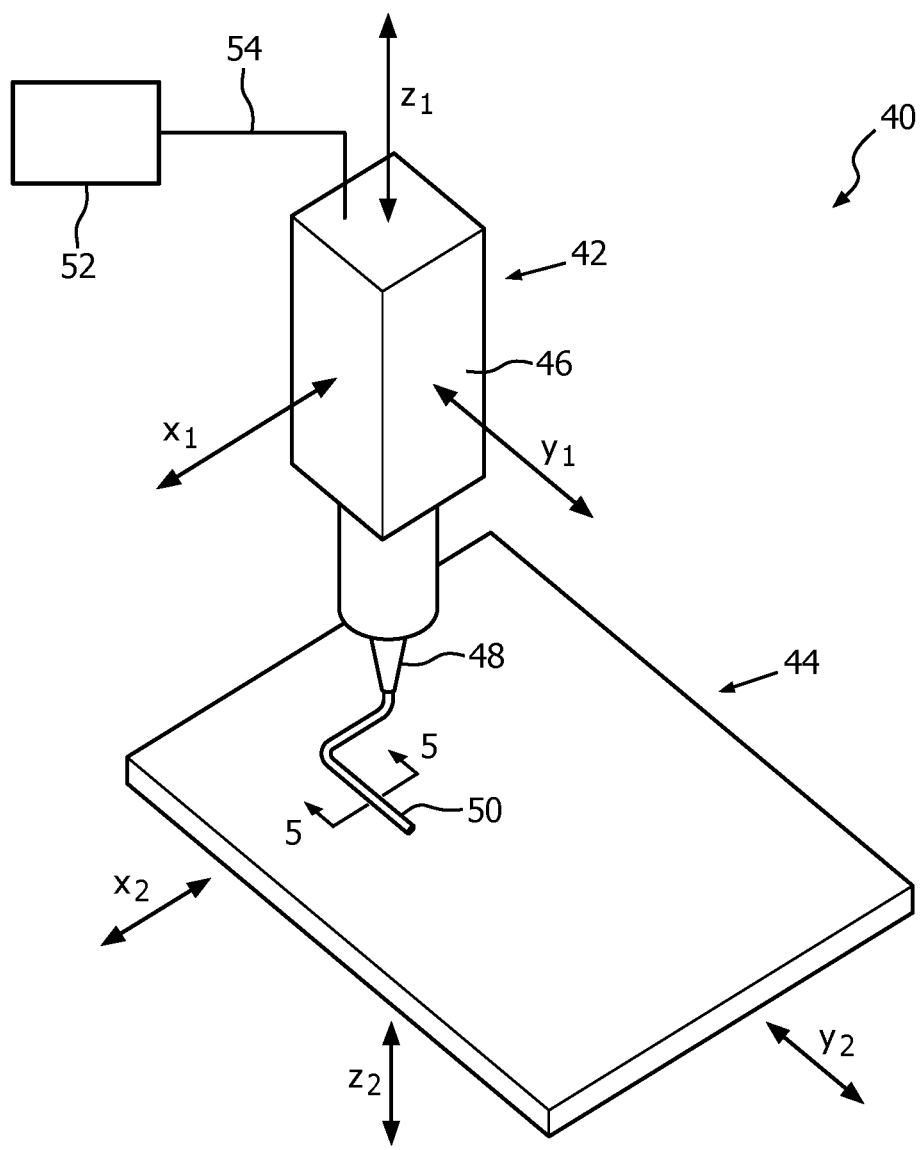
FIG. 4 is a partially schematic isometric view of a system for forming a support member shown disposing a bead of material on a work surface according to one exemplary embodiment of the invention.

Referring to FIG. 4, system 40 includes a dispensing unit 42 disposed generally above a work surface 44. Dispensing unit 42 includes a frame or housing 46 having a number of distribution nozzles or ports 48 through which a bead 50 of a selected material may be provided. In example embodiments of the present invention, silicone rubber, either RTV (Room-Temperature-Vulcanizing) or LSR (Liquid Silicone Rubber), have been employed. However, it is to be appreciated that generally any dispensable flexible material may be used, e.g., without limitation, rubber and elastomeric polymer materials, either single component or multiple component.

Figure 5:
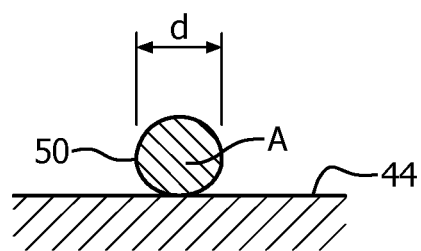
FIG. 5 is a sectional view of the bead of material disposed on the work surface of the system of FIG. 4 taken along line 5-5 of FIG. 4.

FIG. 5 shows a sectional view through an example bead 50 of material disposed on work surface 44. From such view it can be appreciated that such bead has a generally circular cross-section and thus has a cross-sectional area A which can generally be defined by a diameter d. As previously mentioned, it is to be appreciated that other cross-sectional shapes (e.g., without limitation, oval, rectangular, square, etc.) may be employed without varying from the scope of the present invention. Such cross-sectional shapes may be readily selected by varying the shape of the port 48 being used. A supply of material may be provided within housing 46 or may be generally housed in a suitable arrangement 52 external to housing 46 and provided thereto via one or more conduits 54 or other suitable means. It is to be appreciated that although the arrangement shown in FIG. 4 illustrates only a single conduit 54 supplying a single port 48, one or more of the quantity or sizing of such conduit 54 or port(s) 48 may be varied without varying from the scope of the present invention.

Continuing to refer to FIG. 4, dispensing unit 42 may be movable in a predetermined manner along one or more of axis $x_1$, $y_1$ and $z_1$. Alternatively, or additionally, work surface 44 may also be moveable in a desired manner along one or more of axis $x_2$, $y_2$ and $z_2$. Such movements of dispensing unit 42 and/or work surface 44 may be accomplished via the use of any suitable actuating mechanisms, preferably under the control of a computing device. Through such movements of one or both of dispensing unit 42 and work surface 44 while dispensing a bead or beads of material 50, a three dimensional structure may be readily formed on work surface 44. In addition to, and/or instead of, moving along any of axis $x_1$, $y_1$ and $z_1$, one or both of dispensing unit 42 and/or work surface 44 may be rotatable about one or more of any of axis $x_1$, $y_1$ and $z_1$, without varying from the scope of the present invention.

In general, it is to be appreciated that the overall functioning of system 40 is generally similar to a "3D printer". However, unlike a common "3D printer" which employs a moveable heated fusion point that is used to melt feeding material into droplets which are then "printed" on a surface, system 40 utilizes a movable mixing (in case of multi component material) and dispensing unit 42 instead of melting the "printing" material. In system 40, the material is mixed and/or activated (cross-linking) and dispensed as a bead. Depending on the material used, cross-linking may be simply activated when the material comes in contact with ambient air. RTV-1 (single component Room-Temperature-Vulcanizing silicone rubber) is a non-limiting example of such a material which may be used in system 40. Other materials which may be used in system 40 cure by moisture as a base (an aqueous substance that can accept hydrogen ions). Yet further materials which may be used in system 40, e.g., without limitation, RTV-2 (addition cure silicone) or LSR (liquid silicone rubber), can be activated and/or caused to cure faster by applying heat. In such cases, system 40 may further include a heat source (e.g., without limitation, hot air gun, infrared heater, etc.) disposed accordingly to head the material as it is dispensed by dispensing unit 42.

Figure 6:
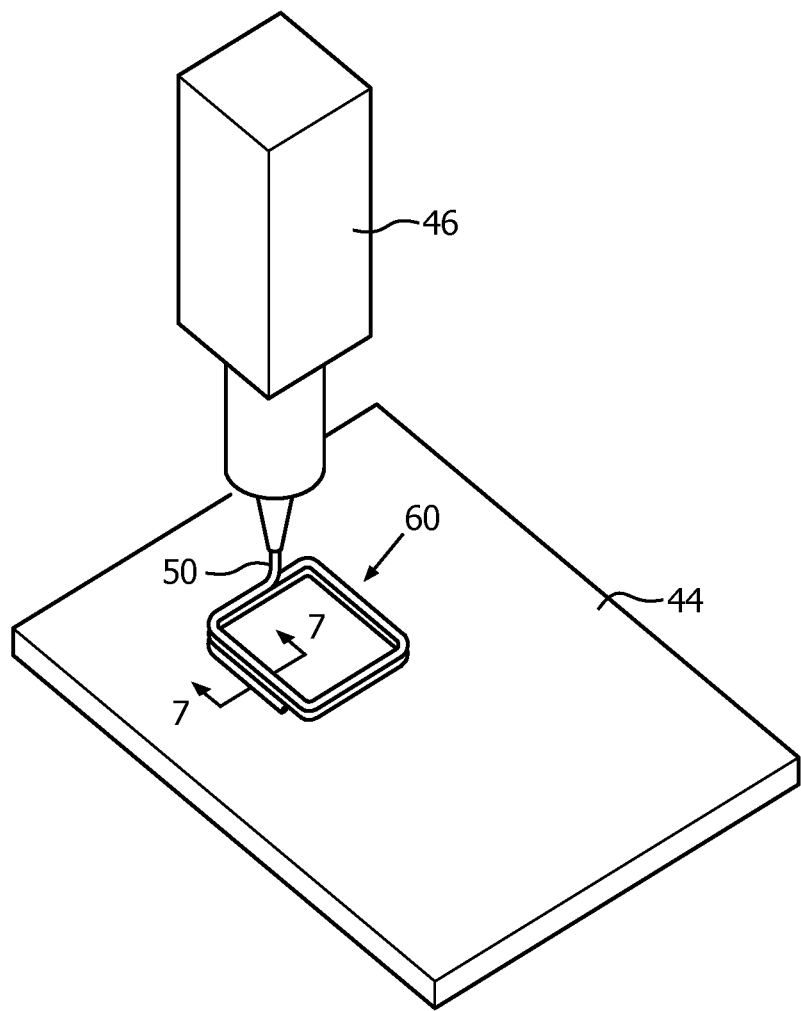
FIG. 6 is another isometric view of the system of FIG. 4 shown further disposing the bead of material on the work surface according to one exemplary embodiment of the present invention.
Figure 7:
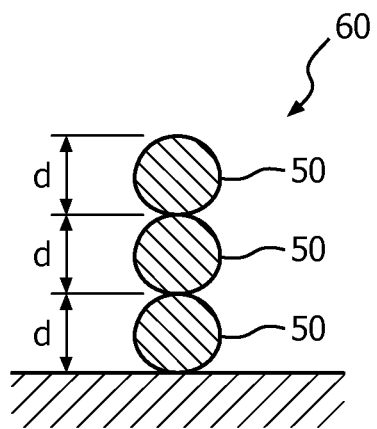
FIG. 7 is a sectional view of the bead of material disposed on the work surface of the system of FIG. 6 taken along line 7-7 of FIG. 6.

FIGS. 6 and 7 illustrate an example of a structure 60 formed on work surface 44 via manipulating one or both of dispensing unit 42 and/or work surface 44 in a manner such as previously described. In such example, structure 60 has been formed by generally stacking three similar beads 50 of material. Although shown generally as a planar surface in FIGS. 4 and 6, it is to be appreciated that work surface 44 may also be provided as a contoured surface, such as work surface 44 shown in FIGS. 8A-8D. From such general description, it is to be appreciated that system 40 may be used to generally form a desired three-dimensional structure from materials which provide for the finished structure to be generally flexible, and thus suitable for use in the sealing assembly of a patient interface device.

Figure 8A:
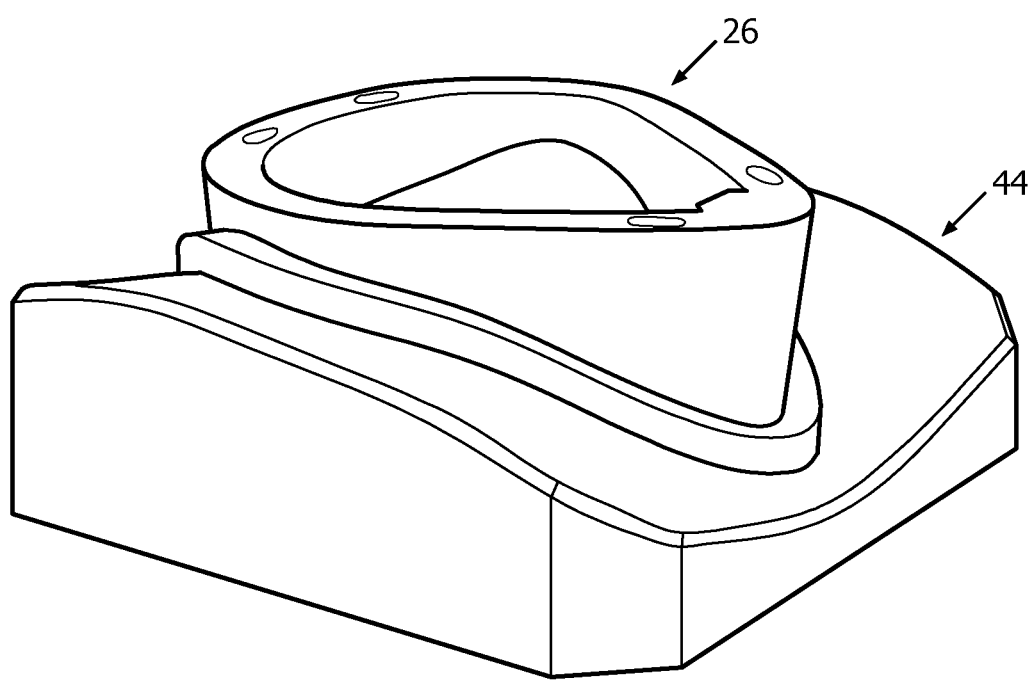
FIG. 8A is an isometric view of a partially formed support member on a contoured work surface of a system such as shown in FIG. 4 according to one exemplary embodiment of the invention.
Figure 8B:
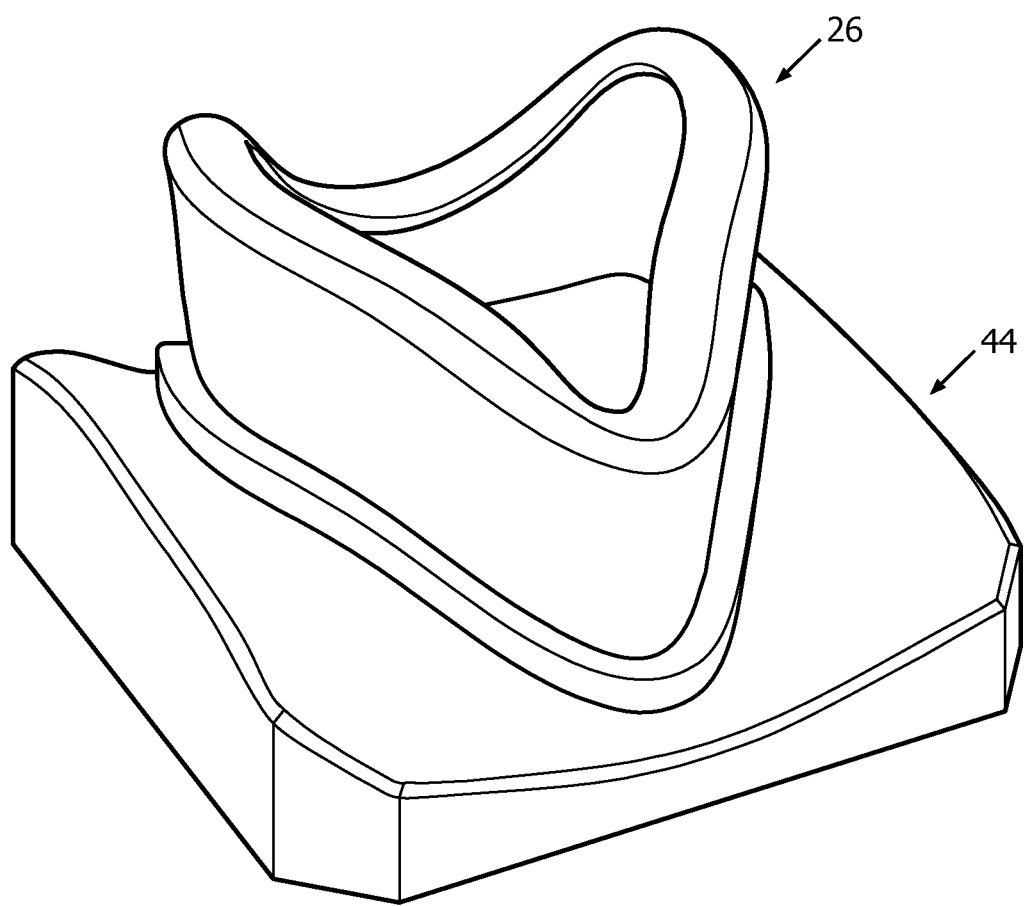
FIG. 8B is an isometric view of a fully formed support member on a contoured work surface of a system such as shown in FIG. 4 according to one exemplary embodiment of the invention.
Figure 8C:
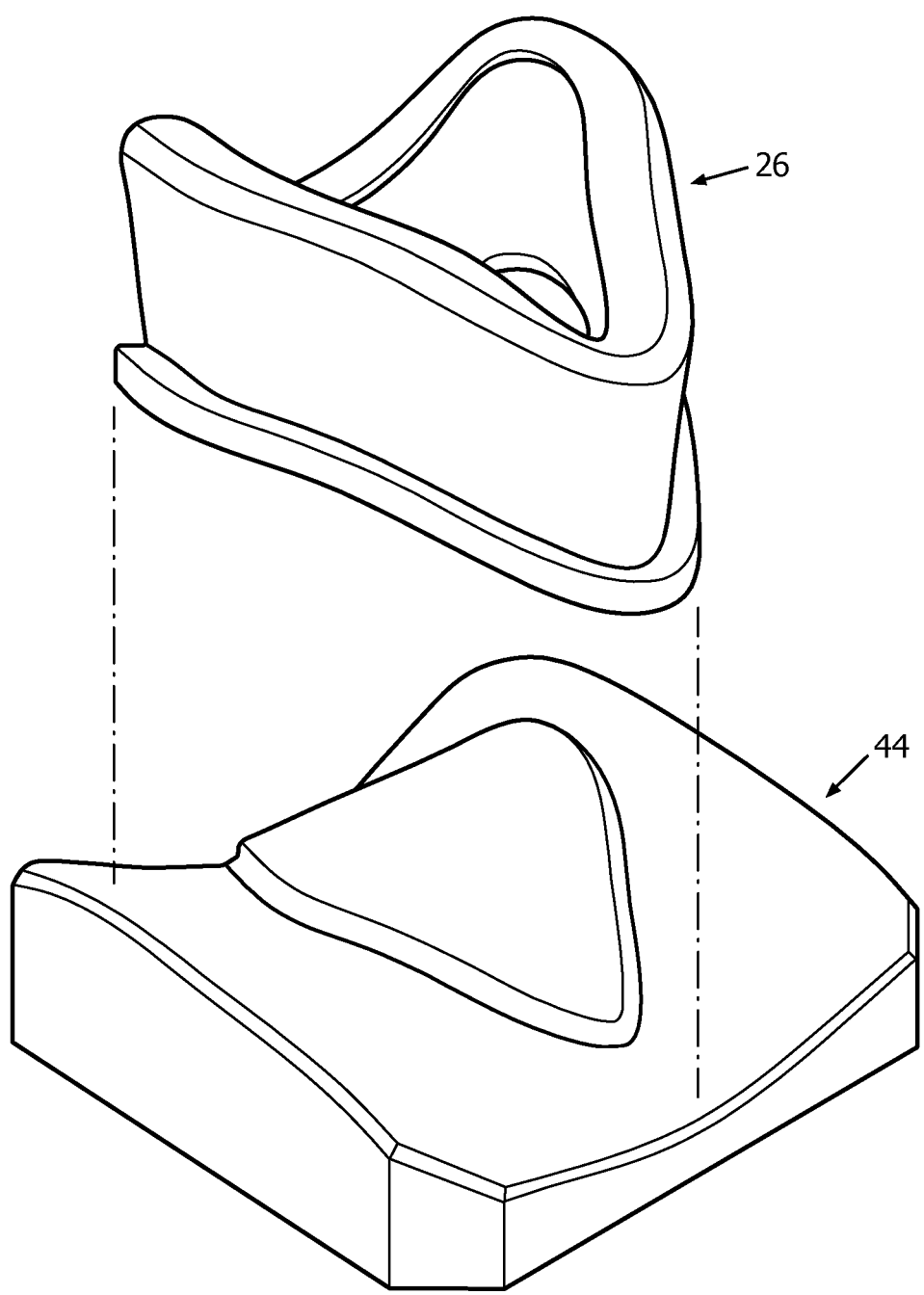
FIG. 8C is an isometric view of the support member and contoured work surface of FIG. 8B showing the support member exploded upward from the contoured work surface.
Figure 8D:
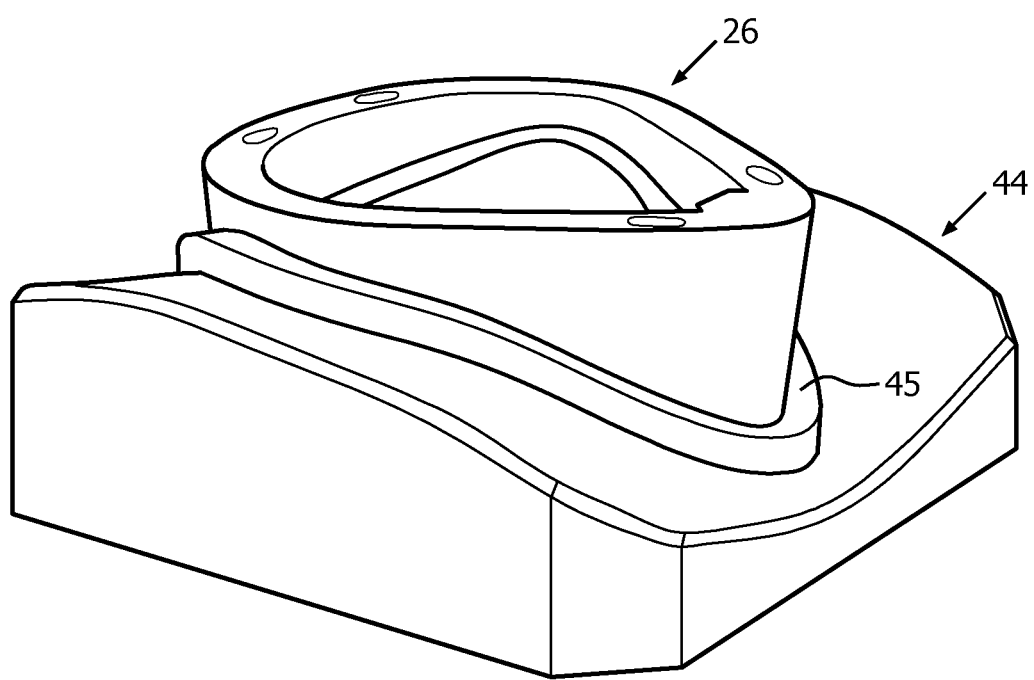
FIG. 8D is an isometric view similar to the arrangement of FIG. 8A except showing a partially formed support member on a pre-molded base which is disposed on the contoured work surface.

FIGS. 8A-8C, respectively, show in simplified form an example support member 26 (as previously described): part way through (FIG. 8A) being formed in a manner as previously described on a contoured work surface 44 of a system 44; completely formed (FIG. 8B) on work surface 44; and separated from (FIG. 8C) work surface 44. Instead of forming support member 26 directly on work surface 44, support member 26 may instead be formed on a pre-molded base 45, such as shown in the example embodiment illustrated in FIG. 8D. Such pre-molded base 45 may be structured to be coupled (e.g., without limitation, via a snap-fit or other suitable arrangement) to frame member 14.

Figure 9A:
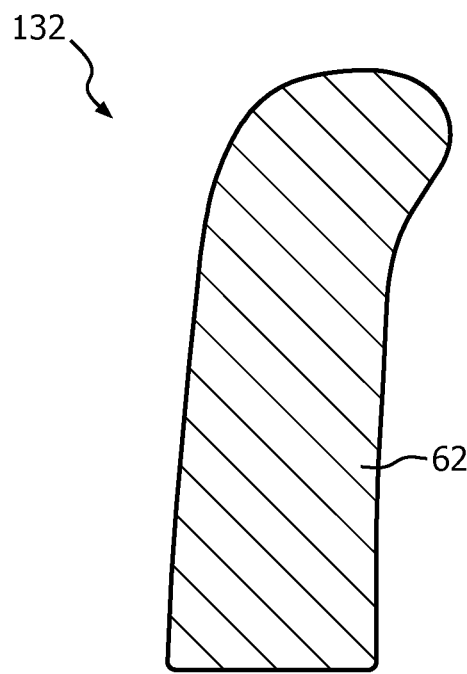
FIGS. 9A-9I are partially schematic sectional views of portions of support members according to exemplary embodiments of the invention.

FIGS. 9A-9I show partially schematic example cross-sectional views of various structural arrangements which may be employed for a portion of side wall 32 of support member 26. More particularly, FIG. 9A shows an example of a sidewall 132 for a support member 26 which was formed via a conventional molding process from a single material 62.

Figure 9B:
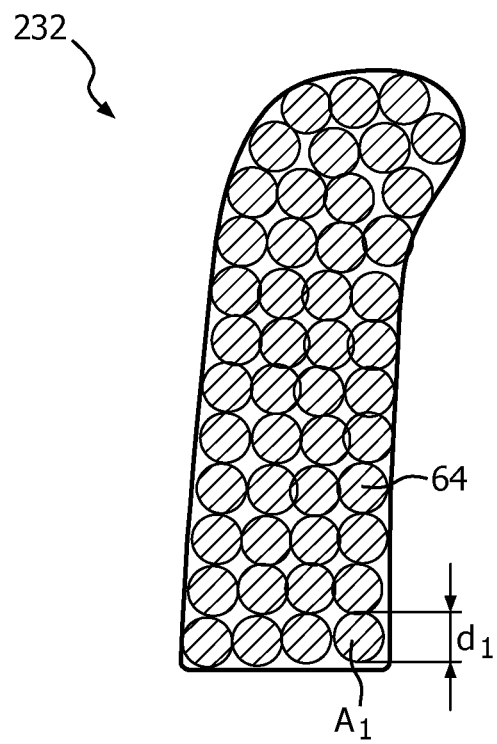

FIG. 9B shows an example of a sidewall 232 formed from a plurality of beads 64 which have been effectively "stacked" using a system such as previously described in conjunction with FIGS. 4-7 and 8A-8D. Each of beads 64 are formed from the same material and are of the same diameter $d_1$ (and thus have the same cross-sectional area $A_1$) which is generally defined by port 48 of dispensing unit 42. In general, a smaller bead size is preferred in detailed areas (i.e., geometrically complex structures that require a higher resolution). For example, in a support member 26 in accordance with the present invention a higher resolution area may require a bead size of 0.25 to 0.50 mm diameter while in a lower resolution area (e.g., without limitation, a straight wall with low curvature) a bead size of 1.0 to 3.0 mm diameter may be desirable.

Figure 9C:
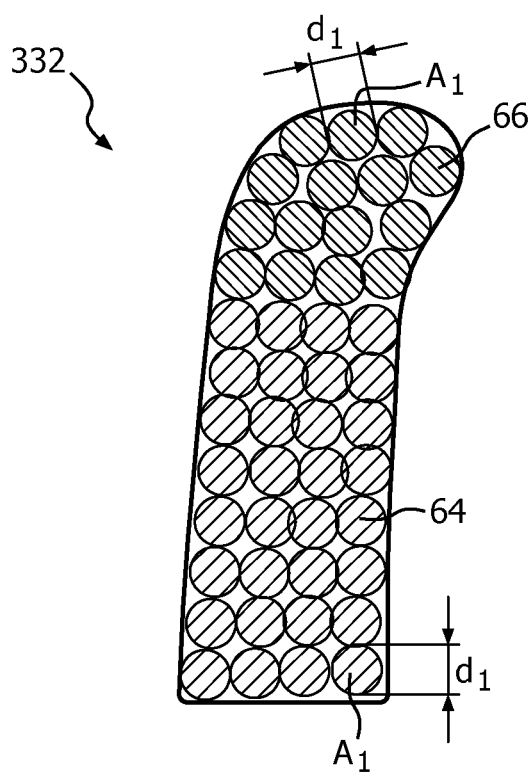

FIG. 9C shows an example of a sidewall 332 formed from a plurality of beads 64, 66 all having the same diameter $d_1$ (and thus the same cross-sectional area $A_1$) similar to the arrangement illustrated in FIG. 9B. However, unlike the arrangement illustrated in FIG. 9B, each bead 64 is formed from a first material and each bead 66 is formed from a second material different from the first material. By utilizing different materials in different locations within sidewall 332 the physical properties of sidewall 332 may be selectively varied. For example, in the example arrangement shown in FIG. 9C, beads 66 may be formed from a material having a lower durometer than beads 64 to provide for a softer end to be disposed adjacent the face of a user while providing a more rigid base for attaching to a frame member.

Figure 9D:
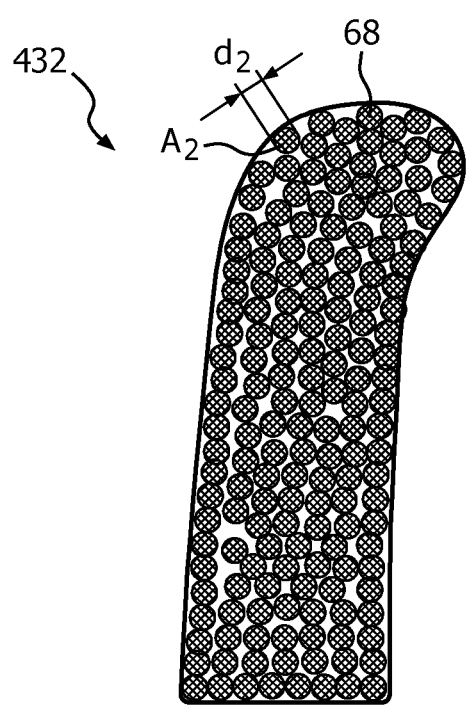

FIG. 9D shows an example of a sidewall 432 formed from a plurality of beads 68 similar to the arrangement shown in FIG. 9B except each of beads 68 is of a diameter $d_2$ (and area $A_2$) smaller than diameter $d_1$ (and area $A_1$) of beads 64. It is to be appreciated that by utilizing smaller bead sizing, higher resolutions in the finished sidewall may be provided. However, smaller bead sizing generally requires longer production time as compared to larger bead sizes.

Figures 9E, 9F:
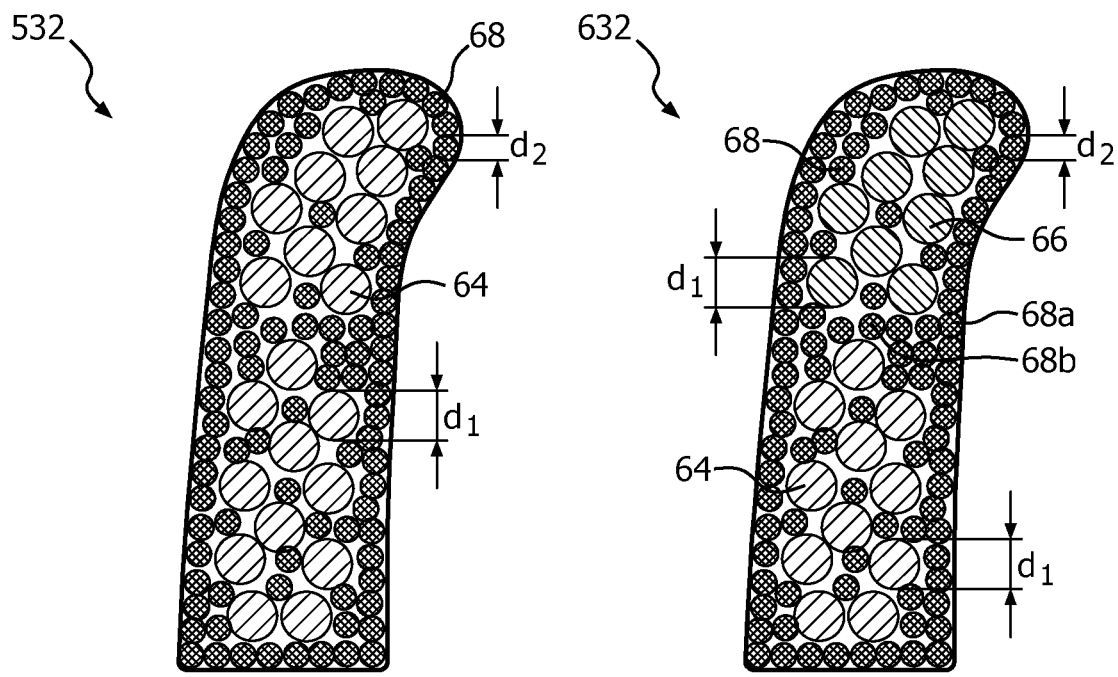

FIG. 9E shows an example of a sidewall 532 formed from a plurality of beads 64, 68 having at least two different diameters $d_1$ and $d_2$ arranged in a predetermined manner. By selectively placing the different diameter beads 64, 68, characteristics (e.g., without limitation, stiffness) of sidewall 532 may be selectively tailored to fit a particular application and more importantly the facial geometry of the patient. In addition, it is to be appreciated that the beads 64, 68 may be formed from the same or different materials in order provide additional selective tailoring of characteristics of sidewall 532.

FIG. 9F shows an example of a sidewall 632, similar to sidewall 532 of FIG. 9E, except sidewall 632 further includes beads 66 of the same diameter $d_1$ as beads 64 but formed from a second material different than the first material. Once again, by selectively placing the different diameter beads 64, 66 and 68, as well as beads formed from different materials, characteristics of sidewall 632 may be selectively tailored to fit a particular application. In addition, it is to be appreciated that selected beads 68a, 68b of beads 68 may be formed from different materials in order to further selectively tailor characteristics of sidewall 632.

Figures 9G, 9H:
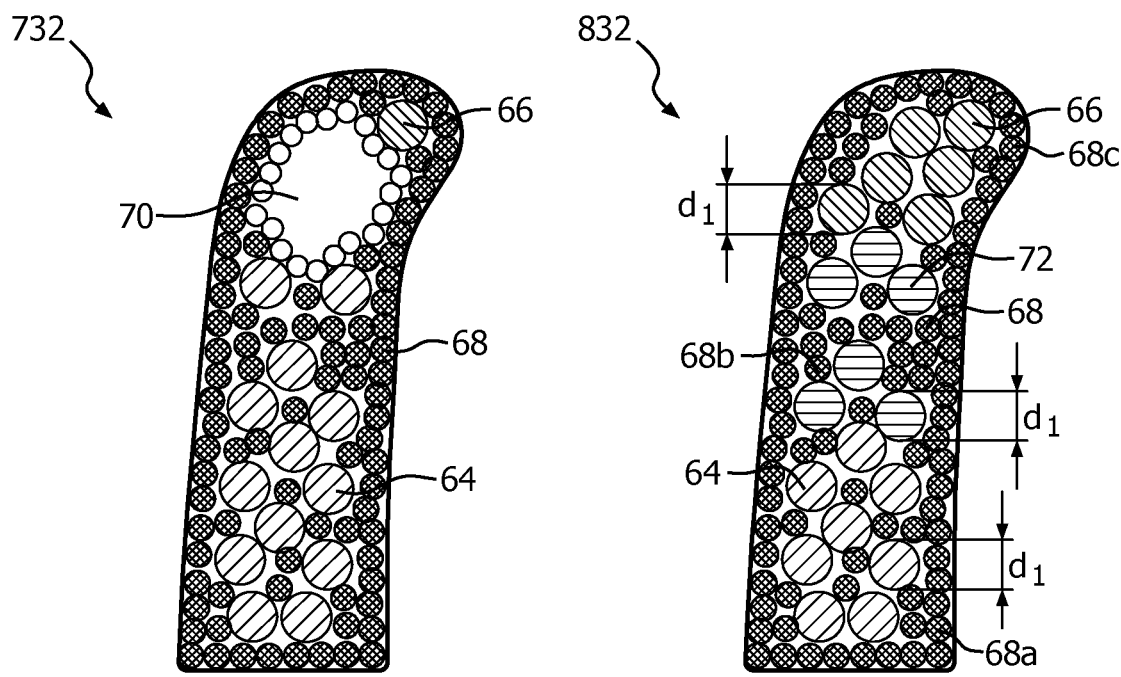

FIG. 9G shows an example of a sidewall 732, similar to sidewall 632 of FIG. 9F, except sidewall 732 further includes a void 70 generally defined by one or more of beads 64, 66, 68. By selectively providing one or more voids 70 within sidewall 732 characteristics of sidewall 732 may be selectively tailored to fit a particular application. More particularly, such voids 70 may be used to provide an improved cushioning effect at desired areas to optimize comfort. Additionally, voids 70 may be used to reduce the time and materials needed to form a support member 26.

FIG. 9H shows an example of a sidewall 832, similar to sidewall 632 of FIG. 9F, except sidewall 832 further includes beads 72 of the same diameter $d_1$ as beads 64 and 66 but formed from a third material, different from the first and second materials. Once again, by selectively placing the different diameter beads 64, 66 and 68, as well as beads formed from different materials, characteristics of sidewall 832 may be selectively tailored to fit a particular application. In addition, it is to be appreciated that selected one or more of selected beads 68a, 68b, 68c may be formed from different materials in order to further selectively tailor characteristics of sidewall 632.

Figure 9I:
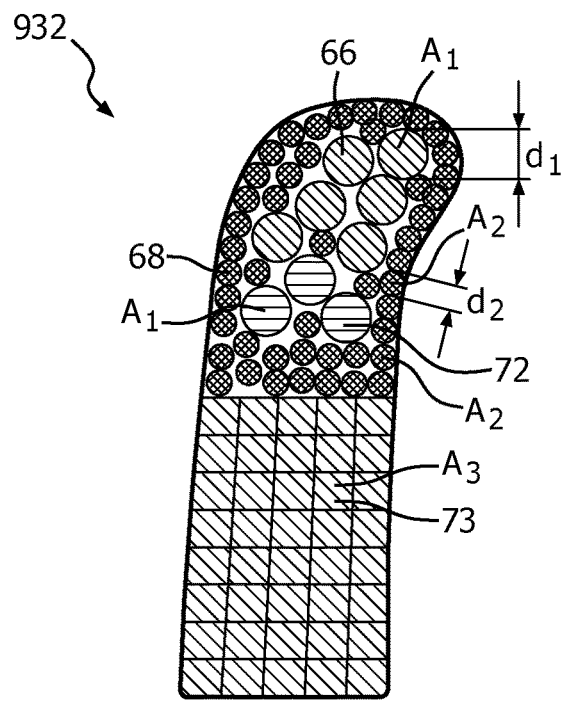

FIG. 9I shows an example of a sidewall 932, which includes beads 66, 68 and 72 having cross-sectional areas $A_1$, $A_2$ which are the same shape but are of different sizes. Beads 66, 68 and 72 are also formed from different materials. Sidewall 932 further includes beads 73 which have a cross-sectional area $A_3$ which is generally square, and thus of different shape than cross-sectional areas $A_1$ and $A_2$ of beads 66,68 and 72.

It is to be appreciated that the particular arrangements shown in FIGS. 9A-9I are provided for exemplary purposes only and that further combinations of differing materials, material sizing, cross-sectional profiles, etc. may be employed without varying from the scope of the present concept. For example, without limitation, materials with a higher tear strength may be employed at boundaries in order to provide tear resistance.

Figure 10:
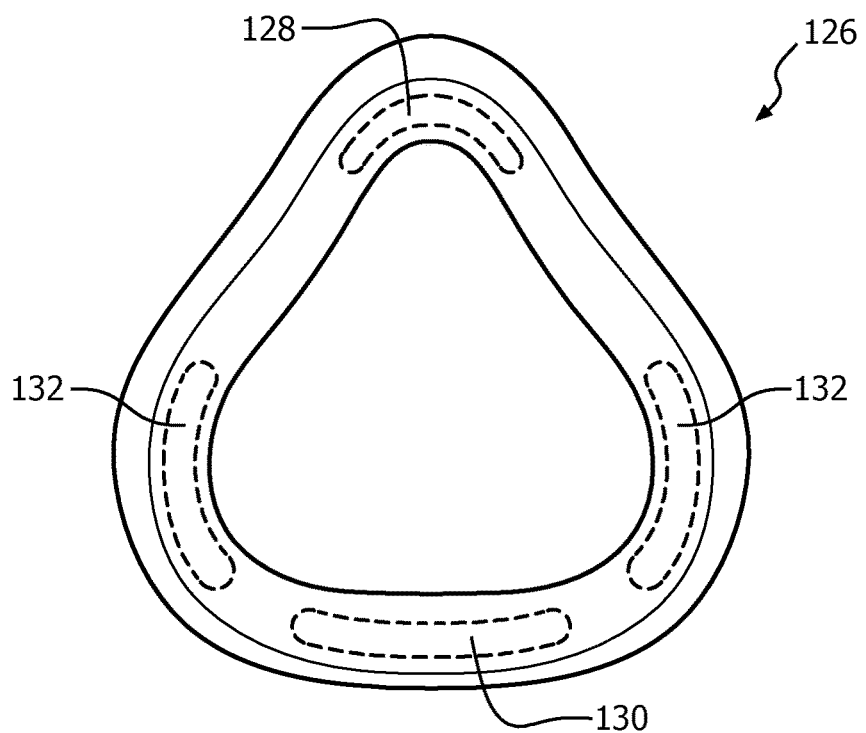
FIG. 10 is an elevation view of the patient facing side of a support member according to one exemplary embodiment of the invention showing (in dashed line) a number of voids formed in the support member.
Figure 11:
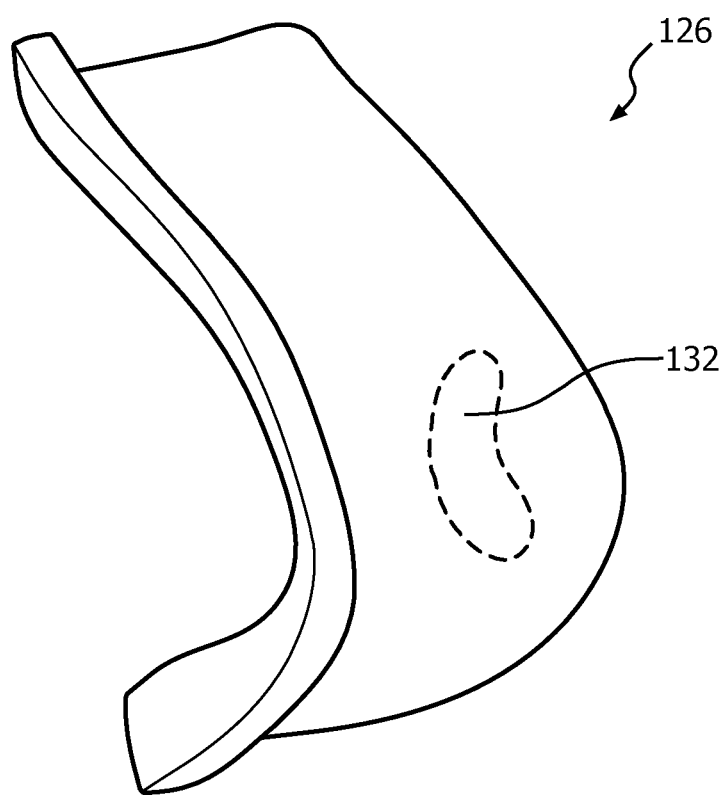
FIG. 11 is a side elevation view of a support member according to one exemplary embodiment of the invention showing (in dashed line) a void formed in the support member.
Figure 12:
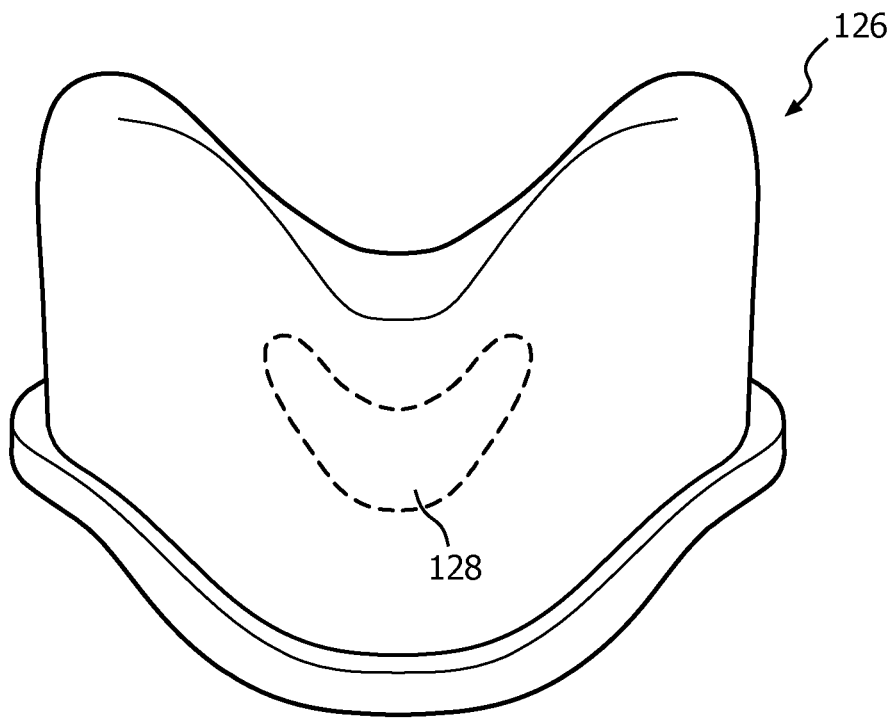
FIG. 12 is a top view of a support member according to one exemplary embodiment of the invention showing (in dashed line) a void formed in the support member.
Figure 13:
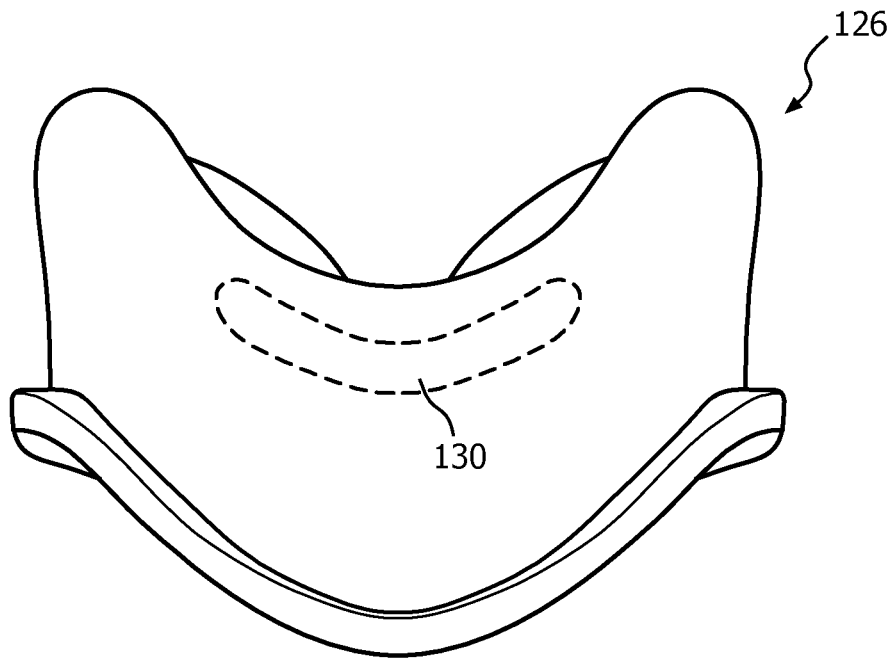
FIG. 13 is a bottom view of a support member according to one exemplary embodiment of the invention showing (in dashed line) a void formed in the support member.

Having thus described example basic structures of components which may be formed in accordance with the present invention, FIGS. 10-13 illustrate examples of the placement of voids, such as previously described in conjunction with FIG. 9G, defined within such structures. More particularly, FIG. 10 illustrates an elevation view of the patient facing side of a support member 126 according to one exemplary embodiment of the invention showing (in dashed line) a number of voids 128, 130, 132 defined in support member 126. Void 128 is defined within support member 126 so as to be positioned near the bridge of a user's nose when support member 126 is disposed in contact with the face of a patient. Void 130 is defined within support member 126 so as to be positioned just below a user's lower lip when support member 126 is disposed in contact with the face of a patient. Voids 132 are defined within support member 126 so as to be positioned generally at or near the sides of a user's mouth when support member 126 is disposed in contact with the face of a patient. FIG. 11 is a side elevation view of support member 126 showing another view of one of voids 132. FIG. 12 is a top view of support member 126 showing another view of void 128. FIG. 13 is a bottom view of support member 126 showing another view of void 130. It is to be appreciated that the example voids illustrated in FIGS. 10-13 are provided for exemplary purposes only and that one or more of the quantity, placement and shape of voids provided may be varied to fit the particular needs of a specific application.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of forming a support member for use in a sealing assembly of a patient interface device for delivering a flow of a breathing gas to the airway of a patient, the method comprising:
    positioning a pre-molded base in a desired positioning:
    dispensing from a port or nozzle a string-shaped first bead of a first settable material extending in a first predetermined pattern on the pre-molded base, the first bead having a first cross-section defined by the port or nozzle; and
    dispensing from the port or nozzle, or from another port or nozzle, a string-shaped second bead of a second settable material extending in a second predetermined pattern adjacent the first bead, the second bead having a second cross-section defined by the port or nozzle or the other port or nozzle,
    wherein the pre-molded base is configured to be directly coupled to a frame member of the patient interface device.

2. The method of claim 1, wherein at least one of:
    the first bead has a cross-sectional area different than the second bead,
    the second settable material is different from the first settable material, or
    the second bead is applied spaced a distance from the first bead so as to form a void there between.

3. The method of claim 1, wherein the first bead consists solely of the first settable material and/or the second bead consists solely of the second settable material.

4. The method of claim 1, wherein at least one of the first bead and the second bead forms a portion of an outer surface of the support member.

5. The method of claim 1, wherein the first settable material comprises a silicone rubber material.

6. The method of claim 1, wherein the first settable material comprises a room temperature vulcanizing material.

7. The method of claim 1, wherein the first settable material comprises a liquid silicone rubber material.

8. The method of claim 1, wherein the first settable material comprises a rubber material.

9. The method of claim 1, wherein the first settable material comprises an elastomeric polymer material.

10. The method of claim 9, wherein the elastomeric polymer material is a single component material.

11. The method of claim 9, wherein the elastomeric polymer material is a multiple component material.

12. The method of claim 1, further comprising molding the pre-molded base via a molding process prior to positioning the pre-molded base.

* * * * *